United States Patent
Inami

[11] Patent Number: 5,905,214
[45] Date of Patent: May 18, 1999

[54] PARTICLE DETECTOR AND PARTICLE ANALYZING APPARATUS

[75] Inventor: Keiichi Inami, Kobe, Japan

[73] Assignee: Toa Medical Electronics Co., Ltd., Hyogo, Japan

[21] Appl. No.: 08/864,118

[22] Filed: May 28, 1997

[30] Foreign Application Priority Data

May 29, 1996  [JP]  Japan .................................. 8-135053

[51] Int. Cl.$^6$ .................................................. G01N 15/02
[52] U.S. Cl. ........................................... 73/865.5; 73/866
[58] Field of Search ................................. 73/865.5, 866, 73/864.85, 864.21, 864.24, 864.22, 64.56; 356/246; 422/63

[56] References Cited

U.S. PATENT DOCUMENTS

| 5,079,959 | 1/1992 | Miyake et al. ........................ 73/864.85 |
| 5,150,037 | 9/1992 | Kouzuki .................................. 73/865.5 |
| 5,412,466 | 5/1995 | Ogino ...................................... 356/246 |
| 5,517,870 | 5/1996 | Kurimura et al. ..................... 73/865.5 |
| 5,690,895 | 11/1997 | Matsumoto et al. .................... 356/246 |

OTHER PUBLICATIONS

"Preparation of Flow Cell For Measuring Specimen"; Patent Abstracts of Japan; Author: Ito Yuji; Publication No.: 60262041 A; Date of publication of application: Dec. 25, 1985; Application No.: 59119413; Date of filing: Jun. 11,1984.

"Flow Cell For Photometry"; Patent Abstracts of Japan; Author: Ito Yuji; Publication No.: 61035333 A; Date of publication of application: Feb. 19, 1986; Application No.: 59158515; Date of filing: Jul. 28, 1984.

*Primary Examiner*—Hezron Williams
*Assistant Examiner*—Nashmiya Fayyaz

[57] ABSTRACT

A particle detector includes: a flow cell having two chambers (A) and (B) communicating with each other via a through-hole, the chamber (A) having an inlet for a sheath liquid and the chamber (B) having an outlet for a waste liquid; a sheath liquid supplier; a nozzle for ejecting a particle-containing specimen with a tip portion of the nozzle being disposed at an appropriate position in the chamber (A), the nozzle being disposed coaxially with the flow cell and movable in an axial direction; an air cylinder for reciprocating the nozzle in the axial direction so as to switch between a sheath flow state for allowing the specimen and the sheath liquid to flow through the through-hole and a non sheath flow state for allowing only the specimen to flow through the through-hole; and a pair of electrodes for detecting a particle in the specimen when the specimen passes through the through-hole. Also, a particle analyzing apparatus including the particle detector is disclosed.

18 Claims, 7 Drawing Sheets

PARTICLE DETECTOR AND PARTICLE ANALYZING APPARATUS

BACKGROUND OF THE INVENTION

1. Field of the Invention

The present invention relates to a particle detector and a particle analyzing apparatus. More particularly, the present invention relates to an improved particle detector for detecting the number, the size, and the like of particles in a particle-containing specimen by means of a flow cell and to an improved particle analyzing apparatus for analyzing particles in a particle-containing specimen by means of a flow cell.

2. Description of the Related Arts

Flow cells for analyzing particles in a sample are disclosed, for example, in Japanese Laid-open Patent Application (Kokai) Nos. Sho 60(1985)-262041 and Sho 61(1986)35333.

In analyzing particles contained in a whole blood sample by means of a known flow cell, three kinds of diluted specimen, namely, a specimen for measuring leukocytes, a specimen for measuring erythrocytes plus platelets, and a specimen for measuring hemoglobin, are prepared out of the whole blood sample so as to measure the number of leukocytes, the number of erythrocytes plus the number of platelets, and the concentration of hemoglobin, respectively in detecting sections each fabricated exclusively for measuring one of the above three kinds of specimen.

The dilution ratio of these three kinds of diluted specimen is, in the case of measuring leukocytes, about 200 to 500 times when a sheath flow is not used, and is about several to 50 times when a sheath flow is used. In the case of erythrocytes plus platelets, the dilution ratio is about 25000 to 50000 times when a sheath flow is not used, and is about 200 to 1000 times when a sheath flow is used. For measuring hemoglobin, the dilution ratio is about 200 to 500 times.

Here, a lot of blood will be required if a specimen is to be diluted in a ratio of about several to 50 times. On the other hand, two diluting steps will be required if a specimen is to be diluted in a ratio of about 25000 to 50000 times.

The two purposes, namely, the reduction of the amount of blood and the simplification of the diluting steps cannot be achieved at a time in a conventional apparatus if the measurement of leukocytes and the measurement of erythrocytes plus platelets are to be carried out in a single detecting section, so that one of these measurements has to be sacrificed. Therefore, two detecting sections are generally provided for carrying out the measurements in the respective detecting sections. This, however, leads to complication of the apparatus and increase in the costs.

SUMMARY OF THE INVENTION

The purpose of the present invention is to provide a particle detector and a particle analyzing apparatus in which plural kinds of particle measurements can be carried out with a measurement specimen prepared by diluting a sample only once.

Accordingly, an object of the present invention is to provide a particle detector comprising: a flow cell having two chambers (A) and (B) communicating with each other via a through-hole, the chamber (A) having an inlet for a sheath liquid and the chamber (B) having an outlet for a waste liquid; sheath liquid supplying means; a nozzle for ejecting a particle-containing specimen with a tip portion of the nozzle being disposed at an appropriate-position in the chamber (A), the nozzle being disposed coaxially with the flow cell and movable in an axial direction; nozzle moving means for reciprocating the nozzle in the axial direction so as to switch between a sheath flow state for allowing the specimen and the sheath liquid to flow through the through-hole and a non sheath flow state for allowing only the specimen to flow through the through-hole; and particle detecting means for detecting a particle in the specimen when the specimen passes through the through-hole.

Another object of the present invention is to provide a particle analyzing apparatus comprising: the particle detector as described above; waste liquid storing means for storing a waste liquid from the flow cell; control means for controlling the nozzle moving means of the particle detector and the sheath liquid supplying means; and processing/analyzing means for processing an electric signal from the particle detected by the particle detecting means of the particle detector and analyzing a data thereof for particle analysis.

DETAILED DESCRIPTION OF THE PREFERRED EMBODIMENTS

Figure 1:
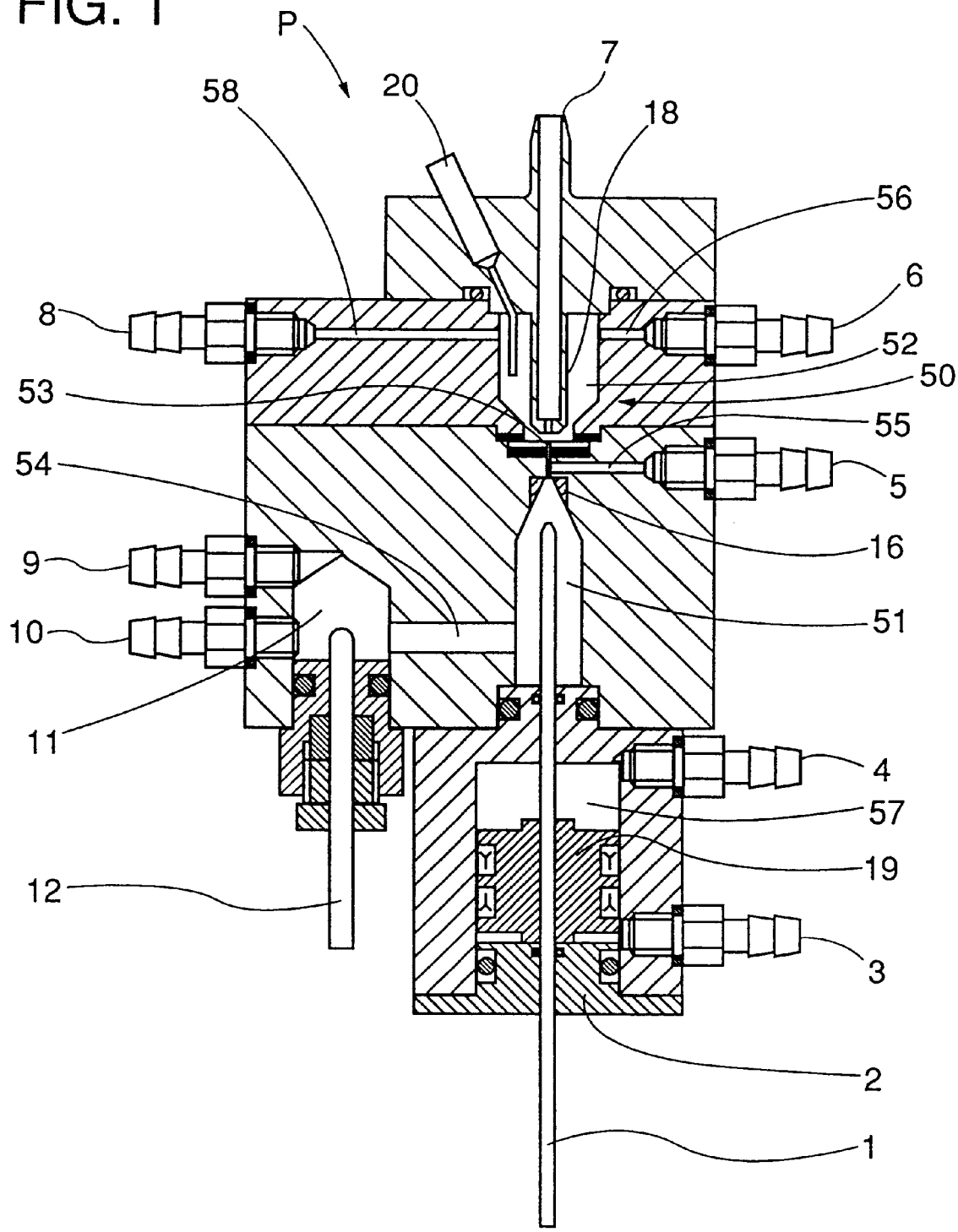
FIG. 1 is an explanatory view for showing a sheath flow state in the particle detector according to the present invention.

The nozzle provided in one of the chambers of the flow cell in the particle detector according to the present invention is for introducing a particle-containing specimen such as a blood specimen into an (A) chamber for letting the specimen flow through the through-hole. The nozzle is adapted to be capable of reciprocating in its axial direction by means of a nozzle moving means such as an air cylinder. This makes it possible to move the nozzle to a predetermined position by means of a nozzle moving means and to switch between the sheath flow state and the non sheath flow state by starting or stopping supplying a sheath liquid. The through-hole may be integrally formed to communicate with the two chambers or, alternatively, may be formed separately from these chambers.

Preferably, the particle detecting means is formed of a pair of electrodes and the nozzle serves as one of the electrodes. The other of the electrodes is disposed on or in the a (B) chamber. The pair of electrodes is for supplying an electric current to the through-hole of the flow cell and for detecting an electric signal generated when the particle passes through the through-hole. The pair of electrodes is made of, for example, stainless steel or platinum. Since the nozzle serves as one of the electrodes, some of the components in the particle detector can be omitted, thereby compactifying the particle detector and reducing the costs.

It is further preferable that the nozzle moving means is adapted to reciprocate the nozzle in its axial direction between a position where the nozzle is fitted onto a contact site (wall surface) near the through-hole in the (A) chamber of the flow cell and a position where the nozzle is separated away from the through-hole so as to switch between the sheath flow state and the non sheath flow state. Preferably, the contact site may be formed in a tapered shape where a sealing member (e.g., elastic material) is provided for sealing a top part excepting an opening of the nozzle. Alternatively, the sealing member may be disposed around the ejecting mouth portion of the nozzle.

The particle detector according to the present invention is incorporated and used in the particle analyzing apparatus of the present invention.

The sheath liquid supplying means is for supplying a sheath liquid to the flow cell. The sheath liquid supplying means is constructed, for example, with a sheath syringe for sucking and discharging a sheath liquid, a passageway for allowing the sheath liquid to flow therethrough, a valve disposed in the passageway, and the like.

The waste liquid storing means includes, for example, a waste liquid chamber.

The nozzle moving means is, for example, constructed with the following. Namely, the nozzle moving means includes a cylinder, a piston head capable of moving in the cylinder while maintaining air tightness, and a supplying nipple for supplying into the cylinder partitioned by the piston head a fluid for moving the piston head.

Here, the nozzle is preferably configured to function as a piston rod by being mounted to the piston head of the nozzle moving means.

The control means controls the nozzle moving means and the sheath liquid supplying means so as to allow the nozzle moving means and the sheath liquid supplying means to operate cooperatively. Here, to allow the nozzle moving means and the sheath liquid supplying means to operate cooperatively is to allow these means to switch between the sheath flow state and the non sheath flow state so as to generate a sheath flow and a non sheath flow selectively in the flow cell.

The processing/analyzing means processes an electric signal from the particle detected by the particle detecting means of the particle detector and analyzes a data thereof for particle analysis. For example, the processing/analyzing means measures the number of pulses and the crest value (peak value) of the pulses generated by the impedance change when a particle contained in the specimen passes through the through-hole of the flow cell while being surrounded by the front sheath liquid.

The present invention is now described in detail by way of preferred examples taken in conjunction with the attached drawings, which are not to be construed as being intended to limit the scope of the present invention.

Figure 2:
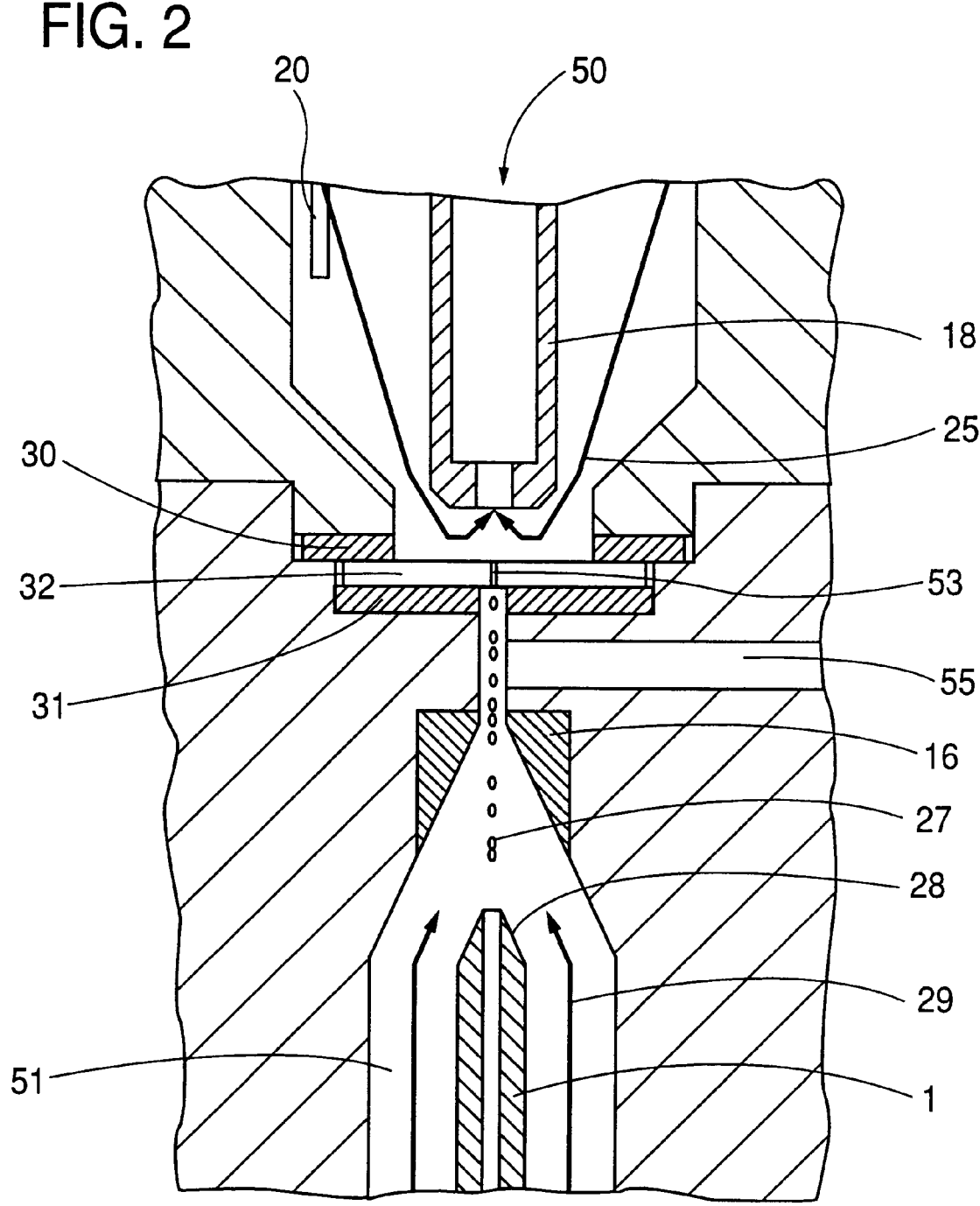
FIG. 2 is an explanatory view for showing an enlarged principal portion of the particle detector in the sheath flow state of FIG. 1.

Referring to FIGS. 1 and 2, the particle detector P according to the present invention includes a flow cell 50 and a pair of upper and lower electrodes 1 and 20. The flow cell 50 includes a first chamber 51 (i.e., corresponding to the chamber (A)) generally shaped like a cylinder and provided, in the upper portion thereof, with a tapered portion and a small diameter portion connected thereto and a second chamber 52 (i.e., corresponding to the (B) chamber) generally shaped like a cylinder disposed above the first chamber 51 and configured to communicate with the first chamber 51 via a through-hole (a small aperture) 53.

The first chamber 51 is provided with an upper end (a tip portion) of the jet nozzle 1 for ejecting the particle-containing specimen and serving as the lower electrode 1. Also, one end of a sheath liquid inlet passageway 54 which forms a part of a sheath liquid supplying means is open to the first chamber 51. The nozzle 1 is made of a stainless steel pipe having an outer diameter of 1.3 mm and an inner diameter of 0.3 mm, with the upper end of the nozzle forming a tapered portion 28. One end of a specimen outlet passageway 55 communicating with a nipple 5 for discharging the specimen is open to a small diameter portion which is located at the uppermost position of the first chamber 51.

The second chamber 52 is provided with a lower end of a sheath liquid collecting tube 18 (a portion of the liquid outlet) communicating with a sheath liquid outlet 7 (a portion of the liquid outlet) which carries outlet flow for waste liquid collection. The second chamber 52 is also provided with a lower end of the upper stainless steel electrode 20. The through-hole (the aperture) 53 is formed at an aperture portion 32 disposed at the interface between the two chambers 51 and 52. The through-hole 53 preferably has a diameter of about 50 to 100 $\mu$m and a length of about 60 to 120 $\mu$m.

The nozzle and electrode 1 and the electrode 20 are for supplying an electric current to the through-hole 53 of the flow cell 50 and for detecting an electric signal generated when the particle passes through the through-hole 53. Namely, they form a particle detecting means.

A nozzle driving section 2 serving as a nozzle moving means is disposed under the first chamber 51. The nozzle driving section 2 is provided with a tubular cylinder 57, a piston head 19 fixed onto a middle portion of the length of the nozzle 1 and configured to slide up and down in the cylinder 57 while maintaining airtightness, and two upper and lower air supplying nipples 3 and 4 for supplying into the cylinder 57 an air for driving the piston head 19. The nozzle 1 is configured to function as a piston rod in the cylinder 57. The nozzle driving section 2 is controlled by a control means (not shown). Namely, the nozzle 1 is driven by the piston head 19 upon receiving the instructions from the control means and is capable of moving up and down in an axial direction in the first chamber 51.

A sealing member 16 is provided around the tapered portion of the first chamber 51. The sealing member 16 is closely fitted onto the tapered portion 28 of the nozzle 1 to seal the tapered portion of the first chamber 51 when the nozzle 1 moves.

An end of a back sheath liquid supplying passageway 56 (a portion of the sheath liquid supplying means) communicating with the back sheath liquid supplying nipple 6 (a portion of the sheath liquid supplying means) is open to the upper portion of the second chamber 52. Also, an end of a bubble-removing passageway 58 communicating with a bubble-removing nipple 8 is open to the upper portion of the second chamber 52.

FIGS. 1 and 2 show a case in which the particle detector P is in a sheath flow state, namely, in which the tapered portion 28 of the nozzle 1 is located at a lower position of the tapered portion of the first chamber 51. In this state, there is a certain distance between the tapered portion 28 of the nozzle 1 and the sealing member 16 as a result of an air for switching to the sheath flow state being supplied from the nipple 4 located at an upper portion of the nozzle driving section 2. When the particle detector P is in the sheath flow state, a sheath flow is formed for the measurement of the particles. The measurement is performed as follows.

Referring again to FIGS. 1 and 2, a diluted specimen introduced from the nozzle 1 to the first chamber 51 is surrounded by a front sheath liquid 29 supplied from a front sheath liquid supplying nipple 10 (a part of the sheath liquid supplying means) through a sheath liquid storing chamber 11 (a part of the sheath liquid supplying means), and the sheath liquid inlet passageway 54 to the first chamber 51. Then, the front sheath liquid 29 forms a sheath flow, which passes through the through-hole 53 of the aperture portion 32 to the second chamber 52. Above the nipple 10 is provided a nipple 9 for removing front sheath bubbles. The tip of a vertically extending thermistor 12 disposed to the left of the nozzle driving section 2 protrudes into the sheath liquid storing chamber 11.

Since the impedance changes when a blood cell 27, a particle in the diluted specimen, passes through the through-hole 53, the number of pulses and the crest value (the peak value) of the pulses generated by this impedance change are measured by a processing/analyzing means (not shown).

The blood cell 27 brought through the through-hole 53 into the second chamber 52 is surrounded by a back sheath liquid 25 supplied from a back sheath liquid supplying nipple 6 (a part of the sheath liquid supplying means) and further flows into the sheath liquid collecting tube 18. As shown in FIG. 2, the aperture portion 32 is held in liquid-tight state by a pair of upper and lower packings 30 and 31.

Figure 3:
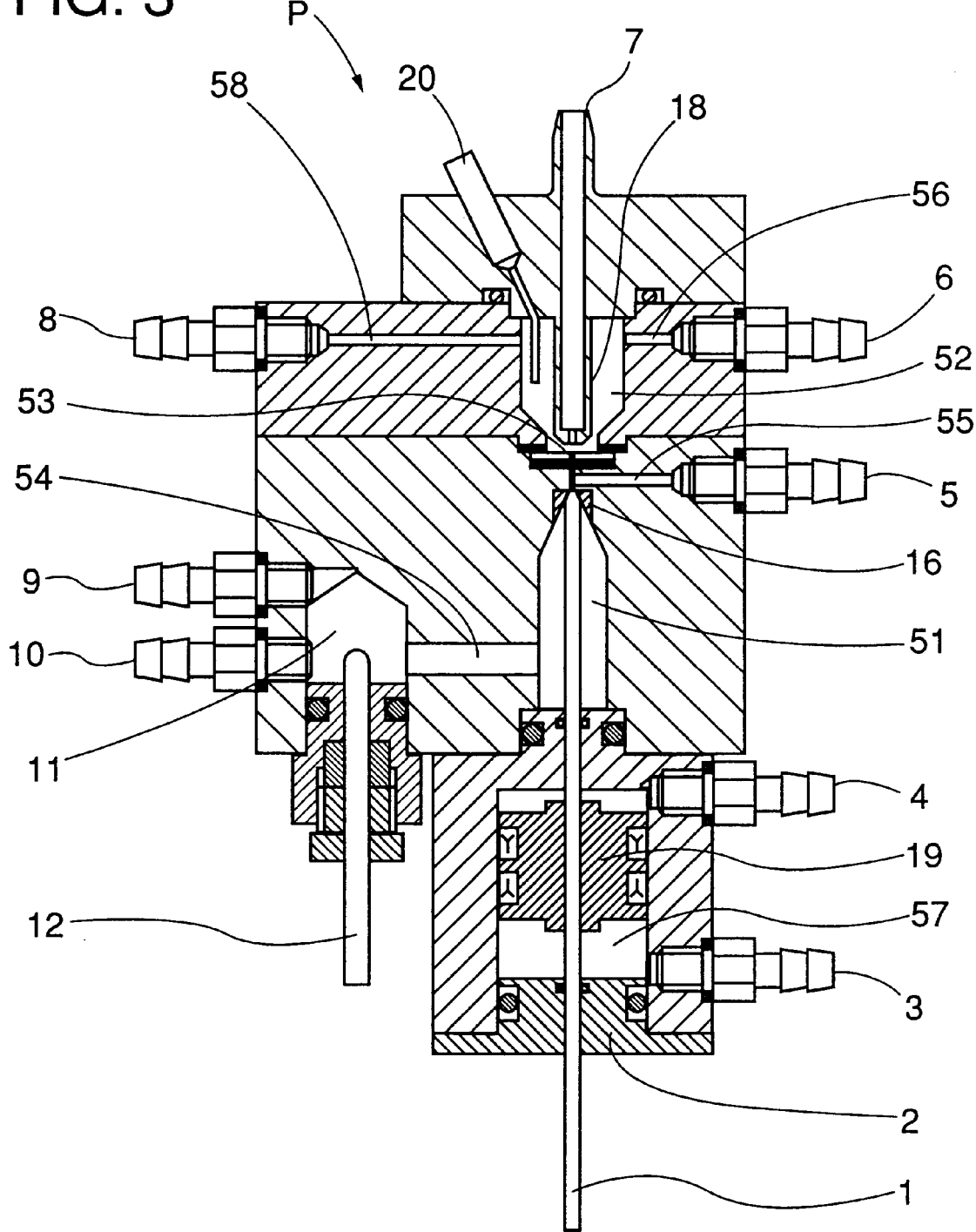
FIG. 3 is an explanatory view for showing a non sheath flow state in the particle detector of FIG. 1.
Figure 4:
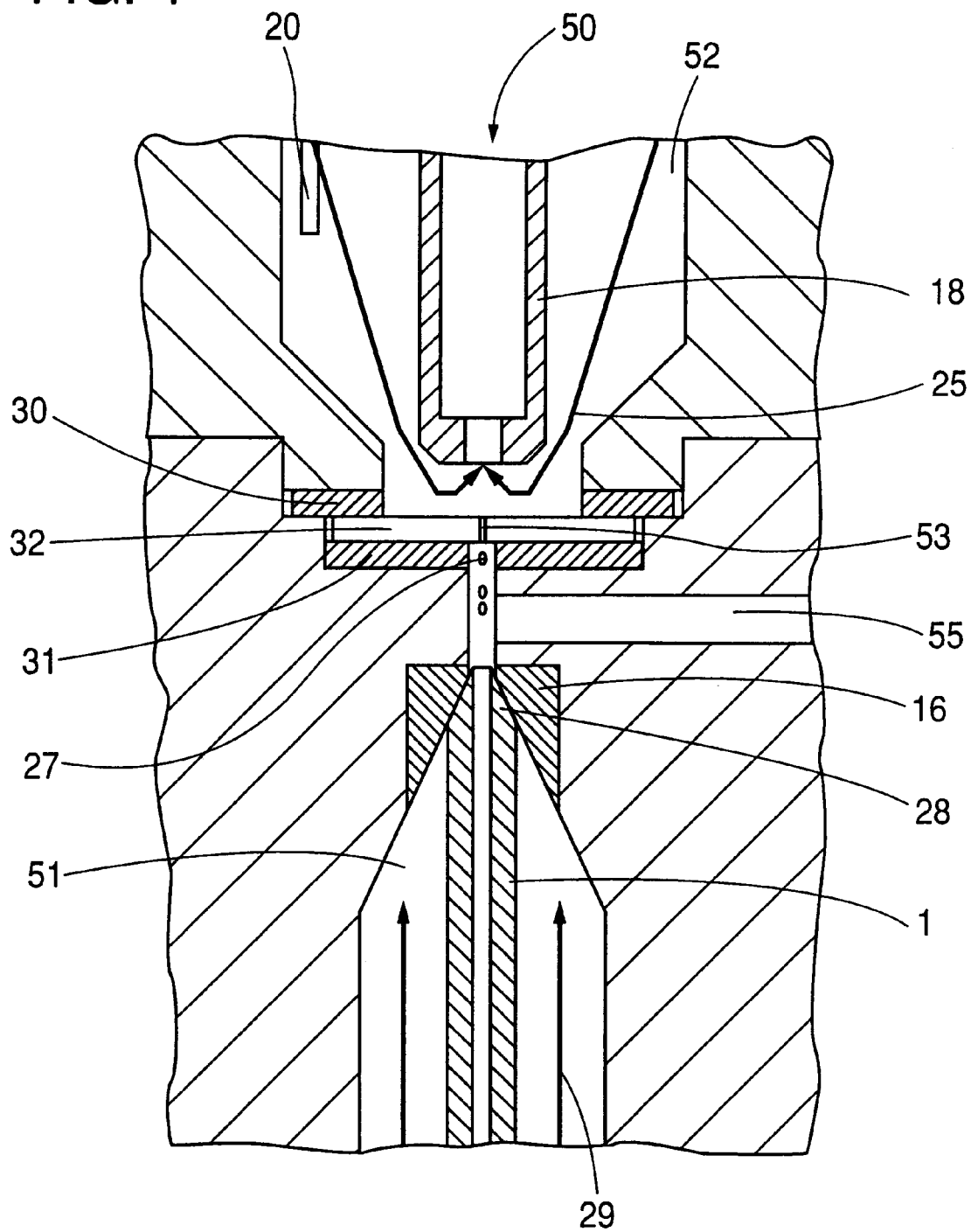
FIG. 4 is an explanatory view for showing an enlarged principal portion of the particle detector in the non sheath flow state of FIG. 3.

FIGS. 3 and 4 show a case in which the particle detector P is in a non sheath flow state, namely, in which the tapered portion 28 of the nozzle 1 fittingly abuts the sealing member 16. In this state, the tapered portion 28 of the nozzle 1 fittingly abuts the sealing member 16 as a result of the upward movement of the piston head 19 caused by an air for switching to the non sheath flow state being supplied from the nipple 3 located at a lower portion of the nozzle driving section 2. This seals the tapered portion of the first chamber 51, allowing the inside of the nozzle 1 to be isolated from the front sheath liquid 29 supplied into the first chamber 51.

In this state, the diluted specimen first flows from the nozzle 1 through the specimen outlet passageway 55 to the nipple 5 for charging so as to replace the existing diluent with the diluted specimen. Afterwards, the blood cells 27 contained in the diluted specimen pass through the through-hole 53 of the aperture portion 32 to flow into the second chamber 52.

Since the impedance changes when the blood cell 27 passes through the through-hole 53, the number of pulses and the crest value (peak value) of the pulses generated by the impedance change are measured by the processing/analyzing means (not shown).

The blood cells 27 that have passed the through-hole 53 to flow into the second chamber 52 are surrounded by the back sheath liquid 25 supplied from the back sheath liquid supplying nipple 6 and flow into the sheath liquid collecting tube 18.

As shown above, the nozzle moving means and the sheath liquid supplying means are operated cooperatively by the control means. Namely, the control means controls the particle detector P so that the sheath liquid flows when the tapered portion 28 of the nozzle 1 is away from the sealing member 16 whereas the sheath liquid does not flow when the tapered portion 28 of the nozzle 1 closely abuts the sealing member 16.

Figure 5:
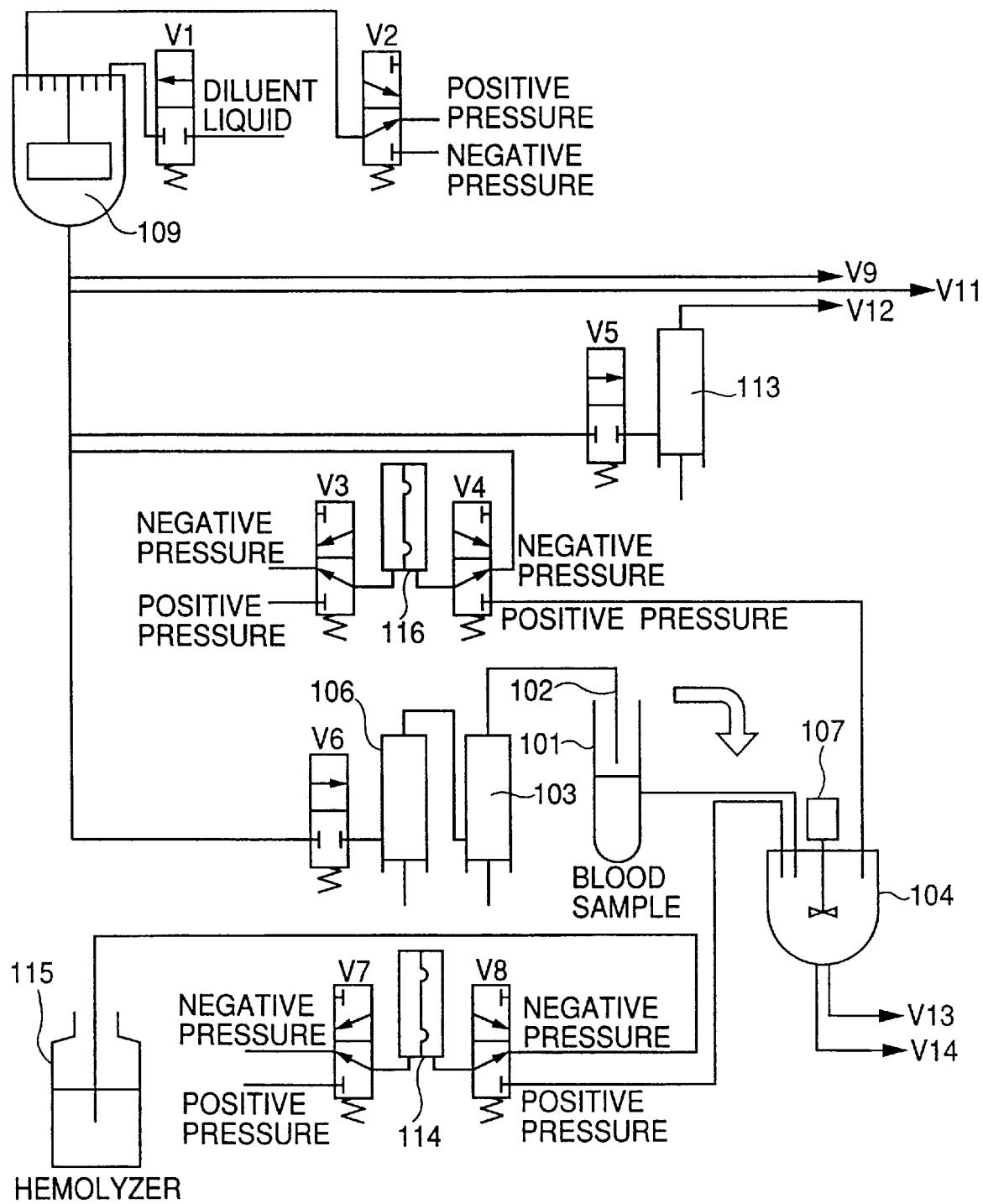
FIG. 5 is a circuit diagram for showing a left side portion of the fluid circuit in the particle analyzing apparatus according to the present invention.
Figure 6:
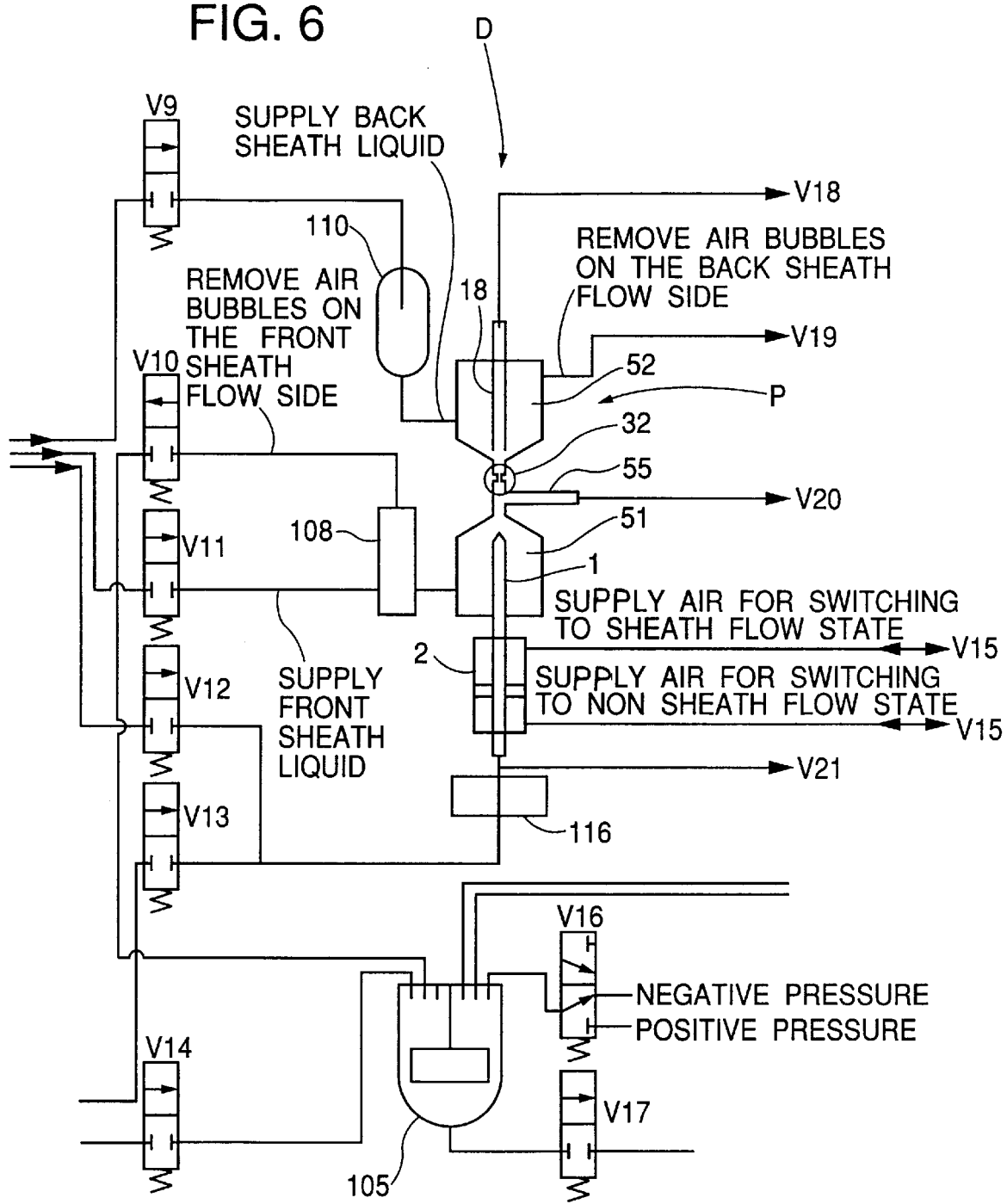
FIG. 6 is a circuit diagram for showing a central portion of the fluid circuit in the particle analyzing apparatus according to the present invention.
Figure 7:
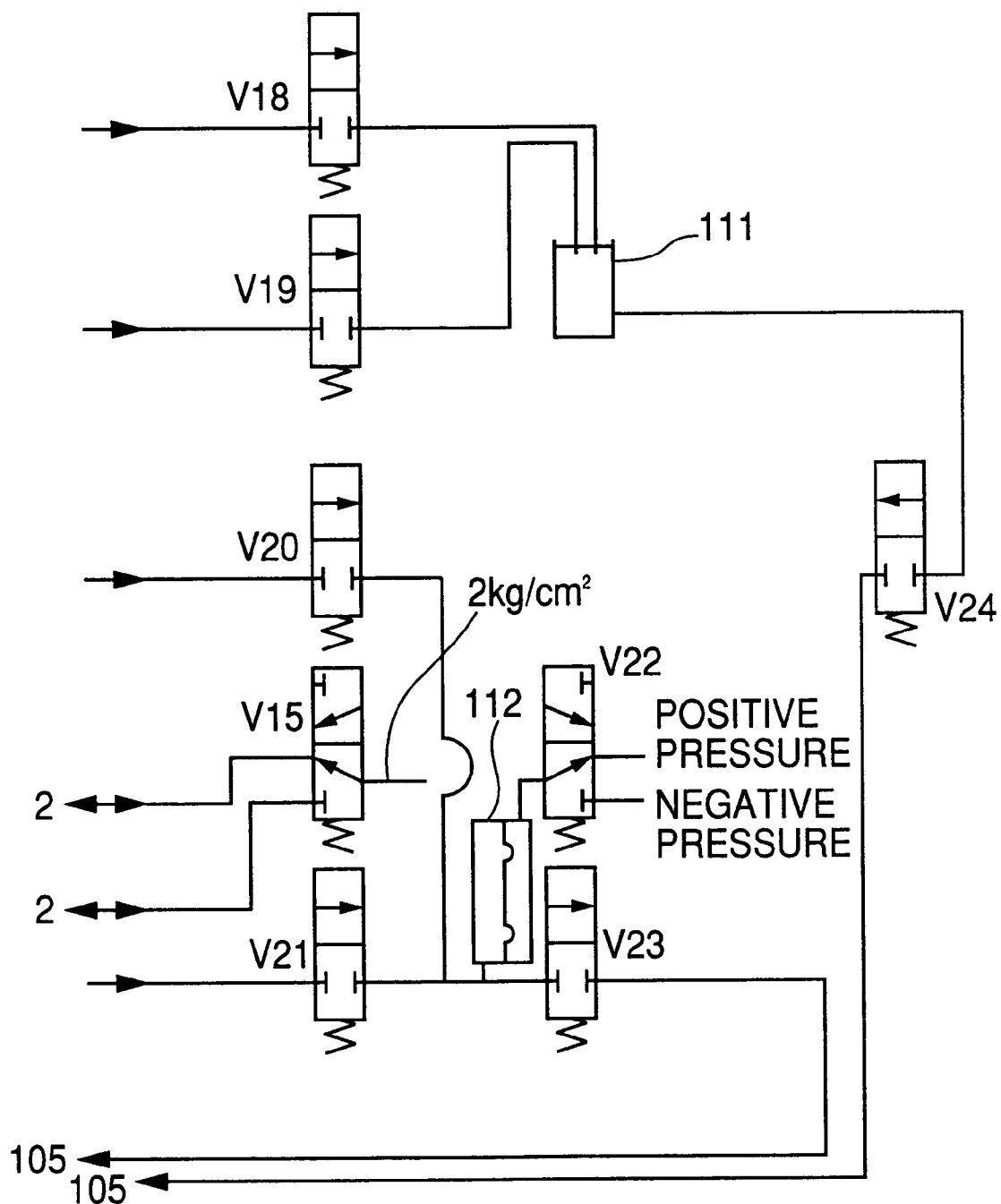
FIG. 7 is a circuit diagram for showing a right side portion of the fluid circuit in the particle analyzing apparatus according to the present invention.

FIGS. 5 to 7 show fluid circuit diagrams of the blood cell counting apparatus which is a particle analyzing apparatus utilizing the particle detector P. The flow of the fluid at the time of measuring the particles is now explained with reference to the fluid circuit diagrams.

Generally, the measurement of the particles is conducted by diluting and mixing the blood sample so as to first measure the erythrocytes plus platelets and then by adding a hemolyzer to measure the leukocytes and the hemoglobin.

First, the diluted specimen is prepared. A specimen sucking pipette 102 is inserted into a specimen container 101 containing blood as the sample to suck 20 $\mu$l of the blood with a blood sucking syringe 103. At the same time, a valve V14 is opened to discharge the diluent liquid pooled in a reaction chamber 104 into a waste liquid chamber 105 serving as the waste liquid storing means. The valve V14 is closed when the discharging operation is finished.

When the sucking of the blood is finished, the pipette 102 is moved to a position above the reaction chamber 104. The blood 17.5 $\mu$l and the diluent liquid 3482.5 $\mu$l are ejected by means of the blood sucking syringe 103 and a diluent liquid syringe 106, respectively. These are mixed by operating a stirring motor 107 to prepare 3500 $\mu$l of a specimen with a dilution ratio of 200 times.

In the measurement of the particles, erythrocytes and platelets are first measured in the sheath flow state. First, air bubbles are removed from a front sheath liquid supplying line and a back sheath liquid supplying line of the particle detector P. Specifically, valves V10 and V11 (a part of the sheath liquid supplying means) are opened to allow the diluent liquid to flow into the waste liquid chamber 105 so as to remove air bubbles present on the front sheath flow side in a bubble removing chamber 108 (sheath liquid storing chamber 11) and in the passageways. Here, the positive pressure applied to a diluent liquid chamber 109 allows the diluent liquid to be forced out of the diluent liquid chamber 109 by only opening the valves V10 and V11. The diluent liquid flows through valve V11→bubble removing chamber 108→valve 10→waste liquid chamber 105, so that there is no particular need to use a pump.

Similarly, a valve V9 (a part of the sheath liquid supplying means), a valve V19, and a valve V24 are opened to remove air bubbles on the back sheath flow side. On this line also, the positive pressure applied to the diluent chamber 109 allows the diluent liquid to be forced out of the diluent liquid chamber 109 by only opening the valves V9 and V19, in the same manner as on the front sheath flow side. The diluent liquid flows through valve V9→first insulating chamber 110 (a part of the sheath liquid supplying means)→second chamber 52→valve V19→second insulating chamber 111, so that there is no particular need to use a pump.

The liquid that has passed through the valves V9 and V19 is pooled in the second insulating chamber 111 for a while, and is sucked by the negative pressure applied to the waste liquid chamber 105 to be discharged through the valve V24 into the waste liquid chamber 105.

Next, the line is charged with the diluted and mixed specimen by means of a specimen sucking pump 112. Here, the specimen sucking pump 112 to be used is adjusted to suck precisely 1500 $\mu$l of the specimen.

After the valves V13 and V21 are opened, the valve 22 is switched to the negative pressure side to suck the diluted specimen out of the reaction chamber 104 by means of the specimen sucking pump 112 so as to fill the passageways with the diluted specimen. Since the specimen sucking pump 112 is adjusted to suck precisely 1500 $\mu$l of the specimen, there will be precisely 2000 µl (i.e. 3500 µl–1500 µl) of the diluted specimen left in the reaction chamber 104.

After the charging is finished, the valves V13 and V21 are closed and, after the valve V23 is opened, the valve V22 is switched to the positive pressure side to discharge the sucked liquid in the specimen sucking pump 112 into the waste liquid chamber 105.

Next, the particle measurement is performed by forming a sheath flow. Namely, the valves V9, V11, V12, V18, and V24 are opened and a sheath syringe 113 (a part of the sheath liquid supplying means) is moved to form a sheath flow for measurement. The sheath liquid supplying means such as the sheath syringe 113 and the valve V11 are controlled together with the nozzle driving section 2 by the aforementioned controlling means.

Specifically, the valve V9 is opened to supply the back sheath liquid, the valve V11 is opened to supply the front sheath liquid, and the valve V12 is opened to move the sheath syringe 113 so as to force out of the nozzle 1 the specimen having charged the line. The valve V18 is opened to discharge the waste liquid from the sheath liquid collecting tube 18 into the second insulating chamber 111. Then, the valve V24 is opened to discharge into the waste liquid chamber 105 the waste liquid which has been discharged into the second insulating chamber 111.

As already shown in FIGS. 1 and 2, the blood cells 27 ejected from the nozzle 1 are surrounded by the front sheath liquid 29 to pass through the through-hole 53 of the aperture portion 32, whereby the processing/analyzing means (not shown) measures the number of pulses and the crest value (peak value) of the pulses generated by the impedance change when the particles pass through the through-hole 53.

When the measurement is finished, the particle detector P and the charging line are cleaned as follows.

First, the ejection operation of the sheath syringe 113 is stopped, and the front sheath liquid 29 and the back sheath liquid 25 are allowed to flow for a certain period of time to let the diluted specimen flowing through the particle detector P to flow out.

Then, the valves V18 and V24 are closed and, at the same time, the valves V21 and V23 are opened to allow the front sheath liquid 29 to flow through the nozzle 1 for a certain period of time, thereby letting the diluted specimen remaining in the nozzle 1 to flow out into the waste liquid chamber 105 so that the nozzle 1 is cleaned.

In this state, the valve V5 (a portion of the sheath liquid supplying means) is opened to allow the diluent liquid forced out of the diluent liquid chamber 109 by the negative pressure to flow for a certain period of time, thereby washing away the diluted specimen remaining in the charging line through the valves V5, V12, V21, and V23.

After the liquid is let to flow for a certain period of time, all of the valves V5, V12, V21, and V23 are closed to finish the cleaning. The valve V5 is closed after the sheath syringe 113 comes to the lower dead point.

Subsequently, water is supplied to the diluent liquid chamber 109 and the waste liquid is discharged out of the waste liquid chamber 105.

Namely, the valve Vi is opened and the valve V2 is switched to the negative pressure side to supply water to the diluent liquid chamber 109. When the floating switch in the diluent liquid chamber 109 is turned on, the valve V1 is closed and the valve V2 is switched to the positive pressure side. Then, the valve V17 is opened and the valve V16 is switched to discharge the waste liquid out of the waste liquid chamber 105. After a certain period of time has passed, the valve V17 is closed and the valve V16 is switched to the positive pressure side to finish discharging the waste liquid.

Subsequently, a specimen for measuring leukocytes and hemoglobin is prepared. A hemolyzer is sucked from a hemolyzer container 115 containing a hemolyzer into a hemolyzer ejecting pump 114 by switching the valves V7 and V8 to the negative pressure side and operating the pump 114. The valves V7 and V8 are then switched to the positive pressure side for ejecting the hemolyzer in the pump 114 into the reaction chamber 104. Simultaneously with the ejection, the stirring motor 107 is operated to mix the diluted specimen remaining in the reaction chamber 104 and the hemolyzer, thereby to hemolyze the erythrocytes.

While the hemolysis is taking place, the particle detector P is switched to the non sheath flow state. Namely, the valve V15 is switched to the non sheath flow side to supply to the nozzle driving section 2 an air for switching to the non sheath flow state. This moves the nozzle 1 upwards to bring the apparatus into a state shown in FIGS. 3 and 4.

In this state, the tapered portion 28 of the nozzle 1 is closely fitted onto the sealing member 16 by being pressed thereto, so that the specimen ejected out of the nozzle 1 is not exposed to the front sheath liquid 29 in the first chamber 51.

Next, leukocytes and hemoglobin are measured. First, the line is charged with the specimen for measuring leukocytes and hemoglobin. Namely, the line is charged with the hemolyzed diluted specimen. The hemolyzed diluted specimen is sucked from the reaction chamber 104 by opening the valves V13 and V20, then switching the valve V22 to the negative pressure side, and operating the specimen sucking pump 112. Then, the passageways on the line from the small diameter portion of the first chamber 51 immediately under the aperture portion 32 to the valve V20 are filled with the hemolyzed diluted specimen through the nozzle 1.

After the charging is finished, the valves V13 and V20 are closed and, after the valve V23 is opened, the valve V22 is switched to the positive pressure side to discharge into the waste liquid chamber 105 the diluted specimen sucked into the specimen sucking pump 112.

Subsequently, the hemoglobin is measured. A hemoglobin measuring section 116 is provided midway on the charged line. A portion of the passageways of the hemoglobin measuring section 116 constitutes a part of the flow cell 50, whereby the hemoglobin can be measured by light absorption method. After the charging is finished, the light absorptivity is measured to determine a concentration of hemoglobin.

Further, the leukocytes are measured. The diluted specimen having charged the line is allowed to flow from the small diameter portion of the first chamber 51 towards the aperture portion 32 by opening the valves V9, V12, and V18 and operating the sheath syringe 113. The blood cells 27 ejected from the nozzle 1 pass through the through-hole 53 of the aperture portion 32. This allows the measurement of the number of pulses and the crest value (peak value) of the pulses generated by the impedance change while the blood cells are passing.

The specimen having passed through the through-hole 53 flows while being surrounded by the back sheath liquid 25 supplied from the line connecting the valve V9, the first insulating chamber 110, and the second chamber 52. The specimen then flows through the sheath liquid collecting tube 18 and the valve V18 and is pooled in the second insulating chamber 111.

The charging line is cleaned and the specimen remaining in the reaction chamber 104 is discharged. The syringe 113 is stopped and the back sheath liquid 25 is let to flow for a certain period of time. At the same time, the valves V13, V21, and V23 are opened to discharge the diluted specimen remaining in the reaction chamber 104 into the waste liquid chamber 105. The valve V13 is closed after all the specimen remaining in the reaction chamber 104 is discharged.

The cleaning of the line connecting the sheath liquid collecting tube 18 and the valve V18 is finished by closing the valve V18. The valve V24 is then opened to suck and discharge the waste liquid pooled in the second insulating chamber 111 into the waste liquid chamber 105. The charging line is then cleaned by opening the valves V5, V12, V20, and V21.

At this time, the sheath syringe 113 is subjected to sucking operation so that the syringe 113 comes to the lower dead point for next measurement. After the cleaning is carried out by letting the liquid flow for a certain period of time, the front sheath side is cleaned by closing the valve V21, opening the valve V11 at the same time, and switching the valve V15 to a sheath flow side to lower the nozzle 1 so that the apparatus comes into the sheath flow state.

After the cleaning is carried out for a certain period of time, all the valves are closed and the cleaning of the charging line and the discharging of the specimen remaining in the reaction chamber 104 are carried out.

Next, the specimen sucking pipette 102 and the reaction chamber 104 are cleaned. Subsequently, the valve V6 is opened for a certain period of time and the diluent liquid is ejected from the pipette 102 and pooled in the reaction chamber 104 for cleaning. The valve V6 is closed when a predetermined amount of diluent liquid is pooled. The mixing blade is cleaned by operating the stirring motor 107. After a certain period of time has passed, the stirring motor 107 is stopped and the valve V14 is opened to discharge into the waste liquid chamber 105 the diluent liquid used for the cleaning of the inside of the reaction chamber 104. The valve V14 is closed after the discharging is finished.

The above operation is repeated for three times to clean the pipette 102, the reaction chamber 104, and the mixing blade.

Next, the diluent liquid is sucked and ejected to be pooled in the reaction chamber 104 by switching the valves V3 and V4 to the positive pressure side and by operating the cleaning liquid ejecting pump 116. Afterwards, the diluent liquid is sucked from the diluent liquid chamber 109 by switching the valves V3 and V4 to the negative pressure side. Next, the charging line is filled with the diluent liquid by opening the valves V13 and V21, switching the valve V22 a little later to the negative pressure side, and operating the specimen sucking pump 112.

Then, the valve V21 is closed and, at the same time, the valve V23 is opened, and the valve V22 is switched to the positive pressure side to discharge the liquid in the pump 112. The valve V23 is closed after the discharging is finished.

Subsequently, water is supplied to the diluent liquid chamber 109 and the waste liquid is discharged from the waste liquid chamber 105.

Namely, water is supplied to the diluent liquid chamber 109 by opening the valve V1 and switching the valve V2 to the negative pressure side. When the floating switch in the diluent liquid chamber 109 is turned on, the valve V1 is closed and the valve V2 is switched to the positive pressure side. Then, the valve V17 is opened and the valve V16 is switched to the positive pressure side to discharge the waste liquid out of the waste liquid chamber 105. After a certain period of time has passed, the valve V17 is closed and the valve V16 is switched to the negative pressure side to finish discharging the waste liquid.

The above process completes a series of measuring steps.

What we claim is:

1. A particle detector comprising:
   a flow cell having (A) and (B) chambers communicating with each other via a through-hole, the (A) chamber having an inlet for a sheath liquid and the (B) chamber having an outlet for outflow of waste liquid;
   sheath liquid supplying means;
   a nozzle for ejecting a particle-containing specimen with a tip portion of the nozzle being disposed at an appropriate position in the (A) chamber, the nozzle being disposed coaxially with the through-hole of the flow cell and movable in an axial direction;
   nozzle moving means for reciprocating the nozzle in the axial direction so as to switch between a sheath flow state for allowing the specimen and the sheath liquid to flow through the through-hole and a non sheath flow state for allowing only the specimen to flow through the through-hole; and
   particle detecting means for detecting a particle in the specimen when the specimen passes through the through-hole.

2. A particle detector according to claim 1, wherein the particle detecting means comprises a pair of electrodes, one of the electrodes being the nozzle and the other of the electrodes being disposed in the (B) chamber.

3. A particle detector according to claim 1, wherein the (A) chamber includes a contact site disposed near an entrance of the through-hole, the contact site being capable of closely fitting with the tip of the nozzle.

4. A particle detector according to claim 3, wherein the contact site is formed in a tapered shape at a position surrounding the entrance of the through-hole.

5. A particle detector according to claim 3, wherein the contact site comprises a sealing member.

6. A particle detector according to claim 3, wherein the nozzle moving means reciprocates the nozzle in an axial direction between a first position and a second position, the first position being such that the tip portion of the nozzle is closely fitted onto the contact site of the (A) chamber to isolate the inside of the nozzle from the sheath liquid in the (A) chamber, the second position being such that the tip portion of the nozzle is away from the contact site of the (A) chamber to release the isolation between the inside of the nozzle and the sheath liquid in the (A) chamber, thereby switching between the sheath flow state and the non sheath flow state.

7. A particle detector according to claim 1, wherein the nozzle moving means comprises a cylinder, a piston head fixed onto a middle portion of the length of the nozzle and configured to slide in the cylinder while maintaining airtightness, and a nipple for supplying into the cylinder an air for driving the piston head, wherein the nozzle is configured to function as a piston rod in the cylinder.

8. A particle analyzing apparatus comprising:
   the particle detector of claim 1;
   waste liquid storing means for storing the waste liquid from the flow cell;
   control means for controlling the nozzle moving means of the particle detector and the sheath liquid supplying means; and processing/analyzing means for processing an electric signal from the particle detected by the particle detecting means of the particle detector and analyzing a data thereof for particle analysis.

9. A particle analyzing apparatus according to claim 8, wherein the sheath liquid supplying means of the particle detector comprises a syringe for sucking and discharging the sheath liquid, a passageway for allowing the sheath liquid to flow therethrough, and a valve disposed in the passageway.

10. A particle analyzing apparatus according to claim 8, wherein the control means allows the nozzle moving means and the sheath liquid supplying means to switch between the sheath flow state and the non sheath flow state so as to generate a sheath flow and a non sheath flow selectively in the flow cell.

11. A particle analyzing apparatus according to claim 8, wherein the processing/analyzing means measures the number of pulses and a crest value of the pulses generated by an impedance change when a particle contained in the specimen passes through the through-hole of the flow cell while being surrounded by a front sheath liquid.

12. A particle analyzing apparatus according to claim 10, wherein the control means does not operate the sheath liquid supplying means when the tip portion of the nozzle moved by the nozzle moving means is at a position isolating the inside of the nozzle from the sheath liquid in the (A) chamber and wherein the control means operates the sheath liquid supplying means when the tip portion of the nozzle is at a position in which the isolation is released.

13. A method for operating a particle detector having (A) and (B) chambers communicating with each other via a through-hole, the steps of the method comprising:

supplying a sheath liquid to the (A) chamber;

ejecting a particle-containing specimen through a nozzle having a tip portion disposed at an appropriate position in the (A) chamber, being disposed coaxially with the through-hole, and being movable in an axial direction; and reciprocating the nozzle in the axial direction to switch between a sheath flow state for allowing the specimen and the sheath liquid to flow through the through-hole and a non sheath flow state for allowing only the specimen to flow through the through-hole; and detecting a particle in the specimen when the specimen passes through the through-hole.

14. The method of claim 13 wherein the reciprocating step includes moving the nozzle tip portion into a close fitting relationship with a contact site disposed near an entrance of the through-hole when the particle detector is switched to the non sheath flow state.

15. The method of claim 14 wherein the nozzle tip portion is moved into a close fitting relationship with the contact site formed in a tapered shape at a position surrounding the entrance of the through-hole.

16. The method of claim 14 wherein the nozzle tip portion is moved into a close fitting relationship with a sealing member at the contact site.

17. The method of claim 14 wherein the nozzle tip portion is reciprocated between a first position and a second position, the nozzle tip portion closely fitted onto the contact site of the (A) chamber in the first position to isolate the inside of the nozzle from the sheath liquid in the (A) chamber, the nozzle tip portion being away from the contact site of the (A) chamber in the second position to release the isolation between the inside of the nozzle and the sheath liquid in the (A) chamber, thereby switching between the sheath flow state and the non sheath flow state.

18. The method of claim 13 wherein the particle detector further includes a cylinder, a piston head fixed onto a middle portion of the length of the nozzle and configured to slide in the cylinder while maintaining air-tightness, and a nipple for supplying air into the cylinder to drive the piston head, and wherein the reciprocating step of the method further comprises operating the nozzle as a piston rod in the cylinder.

\* \* \* \* \*